United States Patent
Atzinger et al.

(10) Patent No.: US 8,023,620 B2
(45) Date of Patent: Sep. 20, 2011

(54) X-RAY ARRANGEMENT WITH A CONVERTER AND ASSOCIATED X-RAY METHOD

(75) Inventors: Franz Atzinger, Nuremberg (DE); Juan Manuel Casso Basterrechea, Majadahonda (ES); Clemens Jörger, Forchheim (DE)

(73) Assignee: Siemens Aktiengesellschaft, Munich (DE)

(*) Notice: Subject to any disclaimer, the term of this patent is extended or adjusted under 35 U.S.C. 154(b) by 207 days.

(21) Appl. No.: 11/974,037

(22) Filed: Oct. 11, 2007

(65) Prior Publication Data
US 2008/0107240 A1   May 8, 2008

(30) Foreign Application Priority Data
Oct. 11, 2006  (DE) .......... 10 2006 048 233

(51) Int. Cl.
*H05G 1/58* (2006.01)
(52) U.S. Cl. .......... 378/116; 378/62; 378/98.8; 378/115
(58) Field of Classification Search ............ 378/8, 16, 378/19, 57, 62, 95, 97, 98.7, 98.8, 108–112, 378/114–116, 207
See application file for complete search history.

(56) References Cited

U.S. PATENT DOCUMENTS

| | | | | |
|---|---|---|---|---|
| 3,916,192 A * | 10/1975 | Schmitmann et al. | .......... | 378/98 |
| 4,160,906 A * | 7/1979 | Daniels et al. | .......... | 378/97 |
| 4,247,777 A * | 1/1981 | Pfeifer et al. | .......... | 378/98 |
| 4,255,662 A * | 3/1981 | Waterkamp | .......... | 378/116 |
| 4,360,731 A * | 11/1982 | Fink et al. | .......... | 378/108 |
| 4,433,429 A * | 2/1984 | Finkenzeller et al. | .......... | 378/98.5 |
| 5,448,614 A * | 9/1995 | Suzuki | .......... | 378/115 |
| 5,848,123 A * | 12/1998 | Strommer | .......... | 378/98.8 |
| 5,917,883 A * | 6/1999 | Khutoryansky et al. | .......... | 378/116 |
| 6,196,715 B1 * | 3/2001 | Nambu et al. | .......... | 378/197 |
| 6,222,907 B1 * | 4/2001 | Gordon et al. | .......... | 378/116 |
| 6,351,518 B2 * | 2/2002 | Yokouchi et al. | .......... | 378/98.3 |
| 6,553,095 B2 * | 4/2003 | Rinaldi et al. | .......... | 378/108 |
| 6,744,912 B2 * | 6/2004 | Colbeth et al. | .......... | 382/132 |
| 6,795,528 B2 * | 9/2004 | Nokita | .......... | 378/155 |
| 6,944,269 B2 * | 9/2005 | Schmitt | .......... | 378/115 |
| 6,950,492 B2 * | 9/2005 | Besson | .......... | 378/5 |
| 7,106,824 B2 * | 9/2006 | Kazama et al. | .......... | 378/16 |
| 7,203,270 B2 * | 4/2007 | Okumura et al. | .......... | 378/16 |
| 7,209,537 B2   | 4/2007 | Popescu | | |
| 7,215,733 B2 * | 5/2007 | Nabatame | .......... | 378/16 |

FOREIGN PATENT DOCUMENTS
DE  102004051820 A1  5/2006

* cited by examiner

*Primary Examiner* — Edward J Glick
*Assistant Examiner* — Thomas R Artman

(57) ABSTRACT

The present invention is an x-ray arrangement for examining patients, having an x-ray source and a digital flat panel detector characterized by a processing unit with a converter with an input possibility for a whole data record of system parameters as input parameters which can be easily adjusted and input by the user for conversion into a whole data record of image chain parameters as output parameters.

20 Claims, 2 Drawing Sheets

X-RAY ARRANGEMENT WITH A CONVERTER AND ASSOCIATED X-RAY METHOD

CROSS REFERENCE TO RELATED APPLICATIONS

This application claims priority of German application No. 10 2006 048 233.6 filed Oct. 11, 2006, which is incorporated by reference herein in its entirety.

FIELD OF THE INVENTION

The present invention relates to an x-ray arrangement for examining patients using an x-ray source and a digital flat-panel detector. The present invention also relates to a method for examining patients using an x-ray source and a digital flat panel detector.

BACKGROUND OF THE INVENTION

X-ray systems are nowadays mostly to be assigned in a dedicated fashion to a clinical application. A distinction is thus made between angiography systems, fluoroscopy systems and radiography systems. The two system groups mentioned first can in such cases cover both dynamic applications as well as single image recording (single shot), whereas single image recordings were previously only possible with radiography systems. Radiography systems are used if single shots are to be taken with a very high resolution, for instance images with fine cracks. With fluoroscopy, up to 60 images per second can be recorded, with it being possible however for only approximately ⅓ of the resolution of images from radiography systems to be achieved. Currently combination systems are used, which combine the fluoroscopy functionality and the single frame shooting function as analog apparatuses into one device. Fluoroscopy uses a camera with a light amplifier, single image recording uses a film.

Separate systems have to be used for fluoroscopy, radiography or Digital Fluoroscopic Radiography (mixture of fluoroscopy and radiography). As mentioned above, image amplification systems with a camera were previously used for fluoroscopy and image recording, whereas analog systems with film or digital systems with flat panel detectors are used for radiography.

Changes to the system operating modes such as image frequency, zoom variables or acquisition mode (fluoroscopy, Digital Fluoroscopic Radiography, radiography) mostly require a change in the operating mode in the flat-panel detector and in the image processing. The system parameters accessible to the user must be translated into image chain parameters in each instance.

The problem thus consists in having to use different x-ray systems with completely different parameterization depending on the desired x-ray method.

SUMMARY OF THE INVENTION

Based on the afore-discussed disadvantages and problems, the object is thus to further develop an x-ray system so that the different recording methods can be realized by means of hardware and that the x-ray system is controlled during all recording methods by means of a set of easily adjustable system parameters. It is also important for the patient to be exposed to as little radiation as possible.

The present object is achieved by an apparatus as well as by a method having the features of the claims. The present invention is advantageous for a series of reasons. The core of the invention is a converter which converts the system parameters into flat-panel detector (FD) image chain parameters. The user only needs to select system parameters, he is not confronted with image change parameters. The user, who is generally used to image amplification systems, by means of which previous fluoroscopy recordings are made, or radiography systems, does not need to adjust the way in which he or she operates.

An image chain consists of an x-ray-receiving unit and a data-processing unit (detector).

The clear separation of system parameters and image chain parameters means that the image chain parameters changing significantly more frequently in a product life span than the system parameters does not present any problem. The background for this is that the image chain parameters are very detector-specific. If the detector changes, the image chain parameters also change.

BRIEF DESCRIPTION OF THE DRAWINGS

The invention is described in more detail below with the aid of the description of a preferred exemplary embodiment, with reference to the drawings, in which.

DETAILED DESCRIPTION OF THE INVENTION

Figure 1:
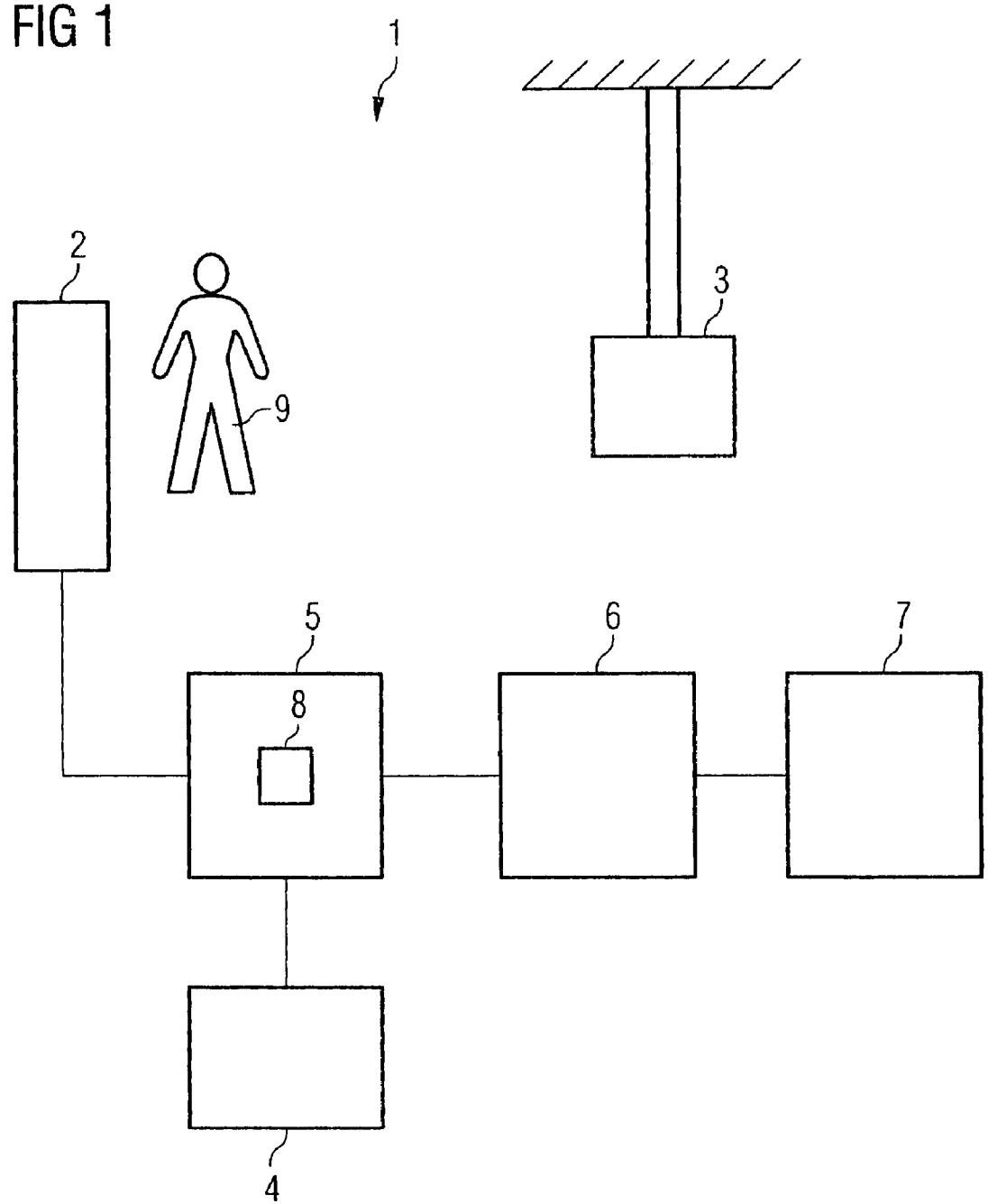
FIG. 1 shows a schematic image of an x-ray arrangement having an x-ray emitter, detector, input unit and a processing unit with converter.

FIG. 1 shows an x-ray arrangement 1 as claimed in the present invention. This is an arrangement 1 for examining patients 9 using flat panel detector technology, with the arrangement comprising an x-ray emitter 3 on the ceiling, a detector 2, an input facility 4, a central control and processing unit 5 with a converter 8, an image processing facility 6 and a monitor 7.

The digital flat panel detector 2 has a readout electronics system, which provides for a cycle consisting of deleting, recording and reading out x-ray information.

The present arrangement 1 is designed to realize the different possible acquisition modes, namely radiography, fluoroscopy Digital Fluoroscopic Radiography and digital subtraction angiography (DSA) using the same hardware and the same set of system parameters. The user inputs system parameters into an input facility 4, namely either as individual parameters, such as zoom for instance, or as a so-called organ program. An organ program contains a whole set of system parameters and facilitates and speeds up the adjustment of the x-ray arrangement. Various predefined organ programs, which can be selected, exist for different body parts or organs to be examined. In such cases the organ programs contain the recording parameters necessary for the recording and the image chain parameters necessary for the image processing. The system parameters are converted in a converter 8, which is designed as part of a central control and/or processing unit 5, into image chain parameters, which control the image chain. The image chain is composed of the detector 2 and the image processing 6 which follows on from the recording of an image. The operation of the x-ray source 2 is also controlled and triggered by the organ programs depending on the desired recording. Depending on the desired recording, the patient 9 is irradiated by means of the x-ray source 3 and the transmitted x-ray light is detected by the digital detector 2, by converting the x-ray light into visible light in a scintillator. The read-out signal is forwarded to the central control/processing unit 5, which feeds the data into an image processing facility 6. After image processing, the examination result is displayed on a monitor 7 as an image. The x-ray arrangement 1 is designed to keep the radiation exposure of the patient as low as possible. This is realized for example in that, unlike previously, continuous fluoroscopy does not take place during fluoroscopy, but instead a pulsed x-ray radiation. Modern digital flat panel detectors are also designed to generate optimal images even with the smallest possible intensity of the x-rays. The sensitivity of the detectors is thus optimized. Intelligent algorithms also contribute to the image processing, in that parameters such as contrast and image intensity are also optimized with a low x-ray dose. Depending on the medical indication, the suitable method, in other words radiography, Digital Fluoroscopic Radiography, fluoroscopy or angiography, is selected. With radiography, individual images are obtained with a high dose, with fluoroscopy, dynamic images (image frequency up to 60 Hz) with a dose per image, which is smaller by a factor 10 than the dose during radiography. Digital Fluoroscopic Radiography (technology) operates in respect of the dose and image frequency in a range between radiography and fluoroscopy. Image frequencies between ½ and 15 are reached. The recording is also referred to as Digital Fluoroscopic Radiography and is a mixture of radiography and fluoroscopy. In this process, a series of single shots are recorded, which are stored. Digital Fluoroscopic Radiography is thus also referred to as stored fluoroscopy. Angiography previously formed part of the fluoroscopy; angiography is nowadays used for purely vascular representation.

A further measure involved in minimizing the x-ray dose for the patient is to limit the x-ray beam to the size of the examination region by using aperture frames with lead plates in the radiation path (not shown in FIG. 1).

Figure 2:
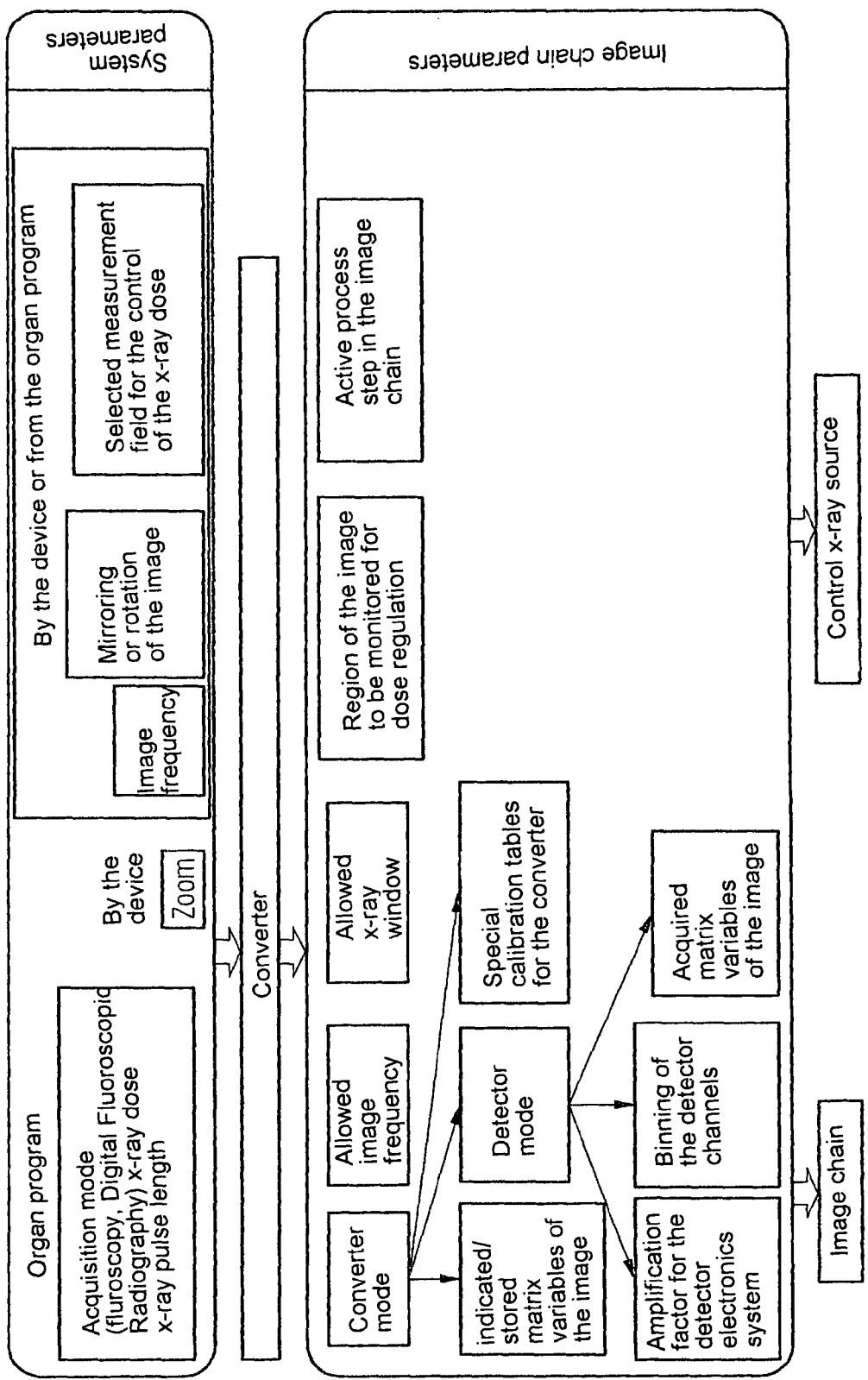
FIG. 2 shows a schematic diagram to explain a method with which specific system parameters are converted into specific image chain parameters.

FIGS. 1 and 2 show a method used to convert system parameters from an organ program into image chain parameters, in order to control the image chain consisting of detector 2 and image processing 6 using the image chain parameters. The operation of the x-ray source 3 is also controlled by an organ program by way of the recording parameters.

The core of the invention is the conversion of a set of system parameters (input parameters), which can be input in a simple manner by the user, into a set of image chain parameters (output parameters). This conversion is carried out by means of the converter 8, in which different output statuses are generated from different input statuses with the aid of tables.

The detailed mode of operation of the converter 8, which can be designed as hardware and/or software, is not the subject matter of the invention claimed here.

The image processing controlled by the image chain is carried out in two stages, namely firstly the generation of a standard image by calculating physical effects in the detector, such as dark current or noise, and secondly the image processing in general. The image chain implements many consecutive steps for each image recording and image processing.

Reference is made below to the system parameters, which the user can select.

As already mentioned above, the acquisition mode can be set as fluoroscopy, Digital Fluoroscopic Radiography or radiography in the form of a predefined organ program. The desired x-ray dose and x-ray pulse length can also be selected by an organ program. Contrastingly, the system parameter zoom must be controlled by direct selection in the device and/or via an organ program. The system parameters image frequency, mirroring or rotation of the image and selected measurement field for the control of the x-ray dose can either be selected by direct selection in the device or by means of an organ program. The measurement field is the image region at which the target dose is to be achieved.

As already described above, the conversion process allows image chain parameters to be generated to control the image chain. Reference is made below to the image chain parameters. The converter mode is a class of image chain parameters, which is dependent on the operating mode of the x-ray arrangement (e.g. fluoroscopy), with the converter mode showing the image chain parameters and determining stored matrix variables of the image, detector mode and special calibration tables for the converter mode, with the detector mode in turn being determined by detector-typical parameters such as amplification factor for the detector electronics system, binning the detector channels and acquired matrix variables of the image.

The matrix variable is the number of pixels in the detector in the x-y direction. Binning allows pixels to be interconnected on the detector, as a result of which a faster read-out of the signals and thus a higher image frequency is possible, this is particularly significant in the case of fluoroscopy and Digital Fluoroscopic Radiography. Noise is also reduced by means of binning. A larger geometric field with a poorer local resolution is produced as a result by means of binning. A matrix size of 1000×1000=1 megapixel to be read out can be effectively generated for instance with a matrix size of 3000× 3000=9 megapixels.

Calibration tables are needed for the converter mode since the changeover of the detector electronics system has weak points. The dark current in the amplifier is removed for instance with the aid of a calibration table.

The amplification factor for the detector electronics system is small in the case of radiography, as a result of the large signal strength and is large in the case of fluoroscopy as a result of the small signal strength.

A further image chain parameter is the allowed image frequency, which triggers the x-ray radiation, with the maximum possible image frequency depending on the process steps and the matrix size and with the allowed image frequency parameter also being required by the arrangement for x-ray generation purposes. A further image chain parameter is the allowed x-ray window, with the length of which depending on the image frequency and the x-ray dose and with the allowed x-ray window parameter also being required by the arrangement for x-ray generation purposes. A further image chain parameter is the region of the image to be evaluated for the dose regulation, with a characteristic being generated which is proportional to the measured dose. A last image chain parameter consists of the active process steps in the image chain, with only specific calibration/correction processes being required per parameter set of a recording. A good single shot with many items of data is important for instance with a radiography recording in contrast to a fluoroscopy recording, as a result of which different data processing steps are needed with radiography than with fluoroscopy. During fluoroscopy, many images are recorded consecutively and some steps are added and some omitted by comparison with radiography.

It is finally worth noting that the converter 8 is equipped with a certain intelligence. Not every combination of system parameters can be translated into image chain parameters for the image chain. System parameter x-ray pulse lengths could have been selected larger for instance than the maximum possible value of the image chain allowed x-ray window parameter. In such a case, the converter 8 corrects the parameters accordingly and gives them back to the system.

The invention claimed is:

1. An x-ray system for acquiring x-ray information of a patient in accordance with a selected one of a plurality acquisition modes, comprising:
   x-ray components including an x-ray source and a digital flat panel detector for recording x-ray information radiographically, fluoroscopically, or Digital Fluoroscopic Radiographically based on a selected acquisition mode;
   an input unit for receiving x-ray system parameters, as individual parameters or as an organ program, wherein the x-ray system parameters comprise a plurality of x-ray dose, x-ray pulse duration, image zoom, image frequency, image mirroring, image rotation, and image region conforming to an acquisition mode different from the selected acquisition mode, and the selected acquisition mode from one of radiography, fluoroscopy, and Digital Fluoroscopic Radiography;
   a control and processing unit in communication with the input unit and the x-ray components for receiving the x-ray information from the digital flat panel detector;
   a converter as part of the control and processing unit for converting the x-ray system parameters from the acquisition mode different from the selected acquisition mode into suitable image chain parameters for the selected acquisition mode that control image recording and image processing based on the selected acquisition mode, the image chain parameters comprising a converter mode as a class of image chain parameters, the converter mode comprising:
      (a) calibration tables for the converter;
      (b) stored matrix variables for the image; and
      (c) detector parameters to control image recording by the digital flat panel detector, all based on the selected acquisition mode; and
   an image processing unit in communication with the control and processing unit for receiving the suitable image chain parameters and processing the x-ray information in accordance with the suitable image chain parameters;
   wherein the selected acquisition mode is realizable with the x-ray components in accord with the selected acquisition mode.

2. The x-ray system as claimed in claim 1, wherein the detector parameters control image recording and the image chain parameters control image processing so that in a radiography mode individual images are obtainable with a relatively high dose, in a fluoroscopy mode dynamic images are obtained at an image frequency up to at least 60 Hz with a dose which is smaller by a factor of 10 than the relatively high dose of the radiography mode, and in a Digital Fluoroscopic Radiography mode images are obtained at a frequency between one half and 15 Hz.

3. The x-ray system as claimed in claim 1, wherein the converter generates a plurality of different output states of the image chain parameter from a plurality of different input states of the x-ray system parameter via a table.

4. A method for acquiring x-ray information of a patient with an x-ray system, comprising:
   receiving x-ray system parameters, as individual parameters or as an organ program, wherein the x-ray system parameters comprise a plurality of x-ray dose, x-ray pulse duration, image zoom, image frequency, image mirroring, image rotation, and image region conforming to an acquisition mode different from a selected acquisition mode, and receiving the selected acquisition mode from one of fluoroscopy, Digital Fluoroscopic Radiography, and radiography via an input unit in communication with a control and processing unit, each acquisition mode realizable with x-ray components comprising an x-ray source and a digital flat panel detector for recording x-ray information radiographically, fluoroscopically, or Digital Fluoroscopic Radiographically based on the selected acquisition mode;
   converting, via a converter as part of the control and processing unit, the x-ray system parameters from the acquisition mode different from the selected acquisition mode into suitable image chain parameters for the selected acquisition mode that control image recording and image processing based on the selected acquisition mode, the image chain parameters comprising a converter mode as a class of image chain parameters, the converter mode comprising:
      (a) calibration tables for the converter;
      (b) stored matrix variables for the image; and
      (c) detector parameters to control image recording by the digital flat panel detector based on the selected acquisition mode;
   adjusting the x-ray components based on the detector parameters for the selected acquisition mode;
   acquiring by the digital flat panel detector the x-ray information in accordance with the selected acquisition mode;
   processing via an image processing unit in communication with the control and processing unit the x-ray information in accordance with the suitable image chain parameters;
   and outputting results of the image processing to a display.

5. The method as claimed in claim 4, wherein the image chain parameter controls the image processing unit after an image recording by the flat panel detector based on the detector parameters.

6. The method as claimed in claim 5, wherein the image processing unit generates an image for output by calculating physical effects in the flat panel detector.

7. The method as claimed in claim 4, wherein the x-ray system parameters correspond to an acquisition mode having parameters determined by the organ program and the acquisition mode is selected from the group consisting of: fluoroscopy, Digital Fluoroscopic Radiography, radiography, and digital subtraction angiography.

8. The method as claimed in claim 7, wherein the fluoroscopy acquisition mode provides continual observation using x-rays up to 60 images/sec for observing a dynamic process in a body of the patient.

9. The method as claimed in claim 7, wherein a recording series is generated by storing images using an x-ray dose between doses used for the fluoroscopy mode and the radiography mode and at an image frequency between ½ and 30 Hz.

10. The method as claimed in claim 7 wherein an image generated by the radiography mode has a higher resolution than that provided by the other modes and is stored separately.

11. The method as claimed in claim 4, wherein the x-ray system parameter requires an x-ray dose or an x-ray pulse length that is determined by the organ program.

12. The method as claimed in claim 4, wherein the x-ray system parameter is selected from the group consisting of: a zoom, an image frequency, a mirroring or rotation of an image, and a selected measurement field.

13. The method as claimed in claim 12, wherein the zoom, the image frequency, the mirroring or rotation of an image, and the selected measurement field are determined by the organ program.

14. The method as claimed in claim 4, wherein the image chain parameter provides a converter mode that determines the image chain parameter and a matrix size of an image.

15. The method as claimed in claim 4, wherein the detector parameters comprise an image parameter amplification factor for detector electronics based on the selected acquisition mode, binning to interconnect pixels of a detector channel based on the selected acquisition mode, and a matrix size of an image based on the selected acquisition mode.

16. The method as claimed in claim 4, wherein the image chain parameter is based on a special calibration table for a converter mode.

17. The method as claimed in claim 4, wherein the image chain parameter is characterized by an allowed image frequency that triggers x-ray releasing and a maximum image frequency depends on image processing and a matrix size of an image.

18. The method as claimed in claim 4, wherein the image chain parameter is characterized by an allowed x-ray window that depends on an image frequency and an x-ray dose.

19. The method as claimed in claim 4, wherein the image chain parameter is determinative of a region of an image to be evaluated for a dose control and a characteristic is proportional to a measured dose.

20. The method as claimed in claim 4, wherein the image chain parameter is determinative of a processing step in an image chain with only specific calibration or correction processes being required per parameter in an image.

* * * * *